(12) United States Patent
Macke

(10) Patent No.: US 10,274,442 B2
(45) Date of Patent: Apr. 30, 2019

(54) ANALYTICAL DEVICE FOR THE ELEMENTARY ANALYSIS

(71) Applicant: C. Gerhardt GmbH & Co. KG, Koenigswinter (DE)

(72) Inventor: Jan Macke, Koenigswinter (DE)

(73) Assignee: C. GERHARDT GMBH & CO. KG, Koenigswinter (DE)

( * ) Notice: Subject to any disclaimer, the term of this patent is extended or adjusted under 35 U.S.C. 154(b) by 327 days.

(21) Appl. No.: 15/191,926

(22) Filed: Jun. 24, 2016

(65) Prior Publication Data

US 2016/0377563 A1    Dec. 29, 2016

(30) Foreign Application Priority Data

Jun. 24, 2015   (DE) .................... 20 2015 004 524 U

(51) Int. Cl.
*G01N 25/22*       (2006.01)
*B01L 3/00*        (2006.01)
(Continued)

(52) U.S. Cl.
CPC .............. *G01N 25/22* (2013.01); *B01L 3/502* (2013.01); *B01L 3/5085* (2013.01); *G01N 31/12* (2013.01); *G01N 35/00029* (2013.01); *G01N 35/00722* (2013.01); *G01N 35/026* (2013.01); *G01N 35/04* (2013.01); *G01N 35/109* (2013.01); *B01L 2200/025* (2013.01); *B01L 2200/026* (2013.01); *B01L 2200/14* (2013.01); *B01L 2300/069* (2013.01); *B01L 2300/0627* (2013.01);
(Continued)

(58) Field of Classification Search
CPC ........ G01N 25/22; G01N 25/20; G01N 31/12; G01N 31/00; B01L 3/502; B01L 3/50; B01L 3/5085; B01L 3/508
USPC .................... 422/78, 68.1, 82.01, 83, 88, 98
See application file for complete search history.

(56) References Cited

U.S. PATENT DOCUMENTS 4,351,193 A    9/1982   Colombo et al.
4,351,801 A    9/1982   Bartke
(Continued)

FOREIGN PATENT DOCUMENTS

DE    2730214 A1    1/1979
DE    3116049 A1    11/1982
(Continued)

OTHER PUBLICATIONS

English Machine Translation of JP 02-098667, Apr. 1990, obtained form https://www4.j-platpat,inpit.go/jp, obtained on Jul. 11, 2018, pp. 1-8. (Year: 1990).*

*Primary Examiner* — Christine T Mui
(74) *Attorney, Agent, or Firm* — The Webb Law Firm

(57) ABSTRACT

The present invention relates to an analytical device for the elementary analysis, which is improved with regard to the feeding of samples, with a sample holder, a line for oxygen and inert gas, a reactor for catalytic combustion of a sample, a reduction reactor that is provided downstream of the reactor, an adsorber that is provided downstream of the reduction reactor, a detector that is provided downstream of the absorber and a logic unit for processing of the data transmitted by the detector, wherein the sample holder includes a perforated field plate that can be moved by means of a drive on a base that is equipped with an ejection opening to eject one of the samples.

15 Claims, 7 Drawing Sheets

(51) Int. Cl.
*G01N 31/12* (2006.01)
*G01N 35/02* (2006.01)
*G01N 35/04* (2006.01)
*G01N 35/00* (2006.01)
*G01N 35/10* (2006.01)
*G01N 31/00* (2006.01)

(52) U.S. Cl.
CPC .... *B01L 2300/0809* (2013.01); *G01N 31/005* (2013.01); *G01N 2035/00099* (2013.01); *G01N 2035/0418* (2013.01); *G01N 2035/0424* (2013.01)

(56) References Cited

U.S. PATENT DOCUMENTS

| | | |
|---|---|---|
| 4,693,867 A | 9/1987 | Commarmot et al. |
| 4,731,335 A | 3/1988 | Brigati |
| 5,395,586 A | 3/1995 | Hemzy et al. |
| 5,571,480 A | 11/1996 | Baccanti et al. |
| 5,612,225 A | 3/1997 | Baccanti et al. |
| 5,866,072 A | 2/1999 | Bowe, Jr. et al. |
| 7,687,029 B2 | 3/2010 | Italiano et al. |

FOREIGN PATENT DOCUMENTS

| | | |
|---|---|---|
| EP | 1586895 A1 | 10/2005 |
| JP | 5624547 A | 3/1981 |
| JP | 5298231 A | 5/1987 |
| JP | 298667 A | 4/1990 |
| JP | 2257062 A | 10/1990 |
| JP | 3062952 U | 7/1999 |
| JP | 2004108862 A | 4/2004 |

\* cited by examiner

US 10,274,442 B2

ANALYTICAL DEVICE FOR THE ELEMENTARY ANALYSIS

CROSS-REFERENCE TO RELATED APPLICATION

This application claims priority to German Patent Application No. 20 2015 004 524.3 filed Jun. 24, 2015, the disclosure of which is hereby incorporated in its entirety by reference.

BACKGROUND OF THE INVENTION

Field of the Invention

The following invention relates to an analytical device for the elementary analysis as it is known for example from the EP 1 586 895 A1. The present invention thereby relates in particular to an analytical device for quantitative elementary analysis. In this context, it aims at indicating in particular an analytical device for the elementary analysis for determining the nitrogen content in a sample.

Description of Related Art

An analytical device for the elementary analysis with a sample holder, a line for oxygen and inert gas, a reactor for catalytic combustion of a sample, a reduction reactor provided downstream of the reactor, an adsorber provided downstream of the reduction reactor, a detector provided downstream of the absorber and a logic unit for processing of the data transmitted is known from the aforementioned EP 1 586 895 A1. The analytical device has a sample holder that is formed by a rotating wheel with a plurality of holes that are arranged on the circumference with an identical radius and at equal distances and that are brought successively over an ejection opening in order to make the sample accessible for the analysis. There, the sample falls into a reactor for catalytic combustion. Therefore, oxygen added for the time of combustion. The quantity of oxygen is calculated automatically in accordance with the sample weight used for calculation and the sample type; consequently, it takes place in a stoichiometric way. Downstream of the reactor, a reduction reactor that is used for the reduction of the sample is provided. Downstream of the reduction reactor, an absorber is provided, which is followed by a detector in order to determine the content of the elements to be analyzed that join the gas flow. The detector interacts with a logic unit to which the data recorded by the detector are transmitted in order to create a usually quantitative evaluation of the sample with regard to the elementary content based on such data.

If, according to the above description, successively arranged components were provided upstream in the flow path of the gas, this shall not mean that no further elements can be arranged in between or behind such components within the analytical device. Hence, as known from the state of the art, a water trap and/or one or multiple self-regeneratable water absorbers can be disposed behind the reduction reactor to extract water from the gas. In addition, a device for regeneration of adsorber elements, which can be extracted cyclically from the gas flow and integrated in the desorption process, can be provided for the separation of the carbon dioxide from the gas flow. This regeneration can be provided outside of a housing of an analytical device that contains a sample holder, a line for oxygen and inert gas, a reactor for catalytic combustion of a sample, a reduction reactor provided downstream of the reactor, an adsorber provided downstream of the reduction reactor, a detector provided downstream of the adsorber, and a logic unit for processing of the data transmitted by the detector. Likewise, the regenerators can also be provided within the housing and be formed in an adapted way for automated desorption as explained for example with EP 1 586 895 A1.

SUMMARY OF THE INVENTION

The present invention aims at further developing the generally known analytical device for the elementary analysis. In this context, it aims in particular at improving the process of inserting samples for the analysis.

To solve this problem, a sample holder that comprises a perforated field plate is proposed with the present invention. The perforated field plate has a plurality of holes that are usually provided in a predetermined grid pattern. The holes are usually formed continuously throughout the perforated field plate, i.e. as throughput holes. They are usually cylindrical. The grid pattern leads to the formation of at least one first hole field in which the holes are usually provided with a constant transversal and longitudinal distance in relation to each other. The perforated field plate is movable on a base that is equipped with an ejection opening to eject a specific sample out of a hole of the perforated field plate. Therefore, the ejection opening usually has a diameter that is equivalent to the diameter of the holes of the perforated field plate in terms of shape and size.

In some examples, an analytical device for elementary analysis is provided, the analytical device comprising a sample holder, a line for oxygen and inert gas, a reactor for catalytic combustion of a sample, a reduction reactor provided downstream of the reactor, an adsorber provided downstream of the reduction reactor, a detector provided downstream of the absorber and a logic unit for processing of the data transmitted by the detector, wherein the sample holder comprises a perforated field plate that is movable on a base by means of a drive, the base comprising an ejection opening to eject one of the samples.

In some examples, a sample holder of an analytical device for elementary analysis is provided, the sample holder comprising a perforated field plate that is movable by means of a drive on a base that is equipped with an ejection opening for ejection of one of the samples.

BRIEF DESCRIPTION OF THE DRAWINGS

The foregoing summary, as well as the detailed description, will be better understood when read in conjunction with the appended drawings. In the drawings.

DESCRIPTION OF THE INVENTION

Figure 1:
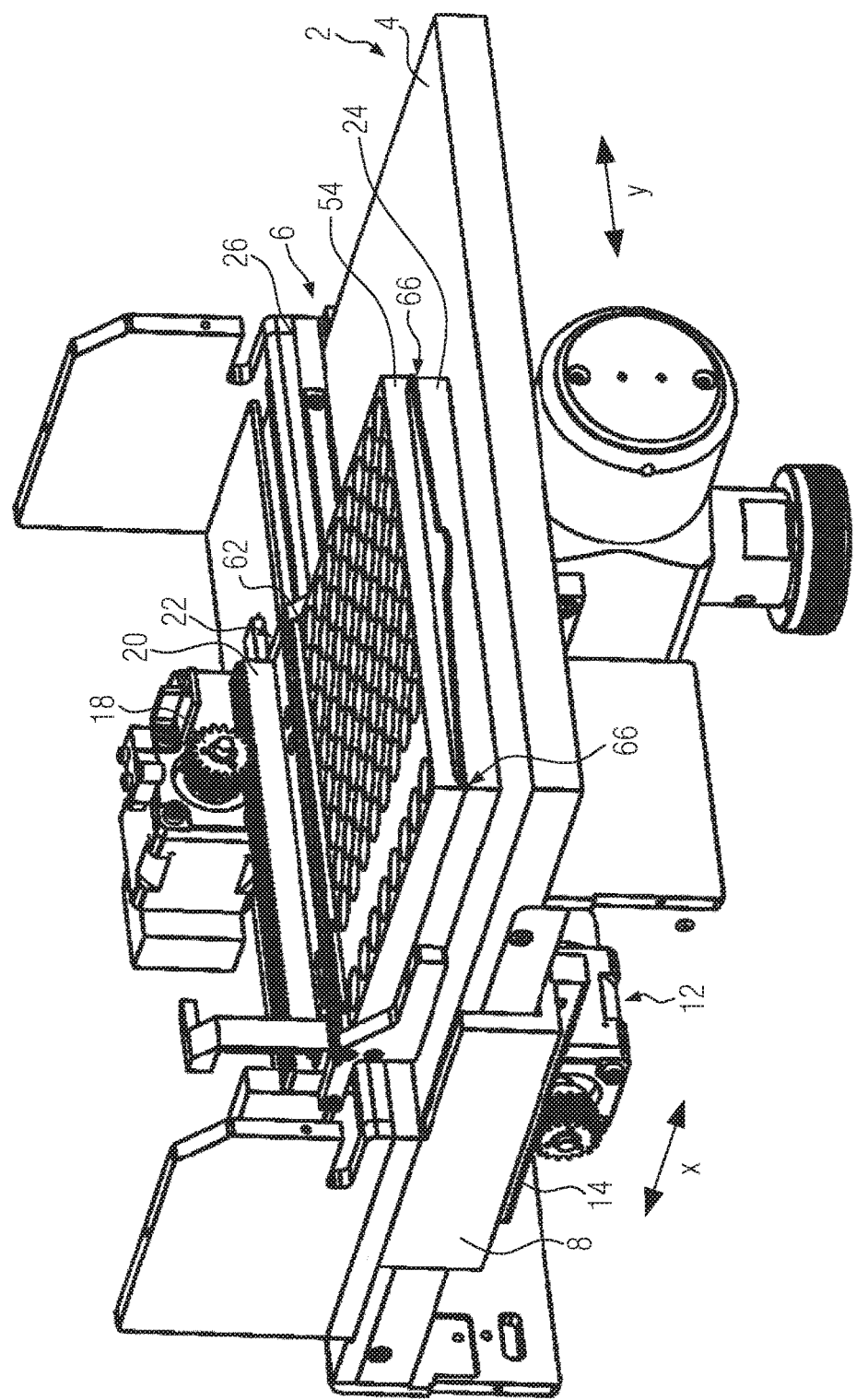
FIG. 1 shows a perspective side view of the top side of an embodiment according to the present invention.

The solution according to the invention allows for filling the perforated field plate with samples from the side that is opposite to the base. The perforated field plate can be moved freely on the base in a regularly translational way, usually in a Cartesian X-Y coordinate system, to bring individual holes of the perforated field plate over the ejection opening and to eject the sample there. In contrast to the previously known solution with a rotating wheel, the previously known solution provides a more flexible possibility to eject samples into the analytical device for the elementary analysis. Therefore, for example the base and the flexibility of the perforated field plate as well as the dimension of the perforated field plate can be harmonized in a way that the perforated field plate can be moved also outside of the ejection opening on the base, i.e. that the individual holes of the perforated field plate can be led past the ejection opening. Due to this, hole fields of the perforated field plate that are positioned differently towards each other can be fed into the ejection opening successively and an overlap with this ejection opening can be ensured. Through the arrangement of the holes and the insertion of the samples into predetermined holes of the perforated field plate, the order for the sample analysis of the individual samples in the holes is therefore not necessarily predefined. Furthermore, there is the possibility to leave out the holes in a predetermined grid pattern that is formed preferably by several parallel rows of holes with preferably identical longitudinal and transversal distances in the perforated field plate, whereby feeding of the perforated field plate with samples is simplified significantly.

According to a preferred further development of the present invention, the perforated field plate has a first hole field and a second hole field that are separated from each other by an enlarged crosspiece. The first hole field usually has a grid pattern with several rows of holes that are located next to each other. This first hole field is used for the usual intake of the sample to be analyzed. The second hole field can comprise few or only one single hole(s). If few holes are provided, these holes of the second hole field can be provided with the same longitudinal or transversal distance to each other as the holes of the grid pattern of the first hole field. However, the second hole field can also be formed by only one single row of holes.

This design comes with the possibility to feed priority samples into the second hole field and to perform the control to move the perforated field plate in relation to the base in a way that a preferred sample outside of the row is targeted. For this purpose, the perforated field plate with its crosspiece is made overlap with the ejection opening and moved along the crosspiece over the ejection opening until the position of the second hole field that contains the sample to be analyzed with preference is reached. The hole that is located at that position will then be made overlap with the ejection opening.

It is clear that the movement of the base in relation to the ejection opening may take place in an automated way by means of drives, preferably in a computer-aided way via a logic unit. This logic unit is usually connected uniformly to the logic unit for processing of the data transmitted by the detector so that the identity of the respectively ejected sample can be transferred directly to the logic unit for processing of the data that is transmitted by the detector.

The enlarged crosspiece usually extends in parallel to two rows of holes that extend in parallel to each other, whereby one row is associated to the first hole field and the other row is associated to the second hole field. Usually, the enlarged crosspiece continues from one edge surface to the other edge surface of the perforated field plate. The crosspiece is enlarged, which means that this crosspiece is wider than the crosspiece between two neighboring rows of holes for example of the first hole field. The crosspiece is usually designed with such a width as to overlap completely with the ejection opening. Hence, the perforated field plate can be moved over the ejection opening without this ejection opening being unblocked even partially, in order to target the prioritized sample of the second hole field and to eject it out of the second hole field.

A particularly simple design of the analytical device is achieved according to a preferred further development of the present invention due to the perforated field plate being held on a crossbeam that can be moved in a first direction in relation to the base. According to this preferred design, the base is formed by a base plate that is encompassed by the crossbeam. Below the base, a drive, which conveys the movement of the perforated field plate through the movement of the crossbeam into the first direction, is preferably provided. This drive can for example be an engine that meshes with the gear rack that is provided on a guide crosspiece of the crossbeam that encompasses the base plate. Guide elements, which guide the movement of the crossbeam in the first direction, are usually provided under the base. Further preferably, the crossbeam has an independent drive that interacts with a holder for the perforated field plate and that moves the perforated field plate along the crosspiece in a second direction. This second direction is the longitudinal direction of the crossbeam and usually extends transversally to the first direction. Through the crossbeam formed this way, the perforated field plate can be moved accordingly in the X-Y coordinate system on the plane of the base. Also the movement in the second direction is usually conveyed by a gear wheel of a drive and a gear rack that extends in parallel to the plane of the perforated field plate and that is coupled with the perforated field plate.

For easier feeding of the perforated field plate, a transfer plate that is equipped with a first transfer hole field that corresponds at least to the first hole field is suggested according to a preferred further development of the present invention. A sliding plate for closing of the transfer plate on the bottom side is assigned to this transfer plate. The sliding plate is usually held in a sliding guide of the transfer plate and secured against falling out in the direction of the transfer holes formed on the transfer plate while being movable in one direction and at a right angle to the former direction. The sliding plate closes the transfer holes left out in the transfer plate on the bottom side. Therefore, the transfer plate can at first be loaded with samples. The transfer plate has form locks or other positioning aids to produce an overlap of the hole fields on both sides of the transfer plate on one hand and of the perforated field plate on the other hand. In this process, the holes of the perforated field plate are usually coded, whereby the coding is provided preferably on the sliding plate so that the individual positions within the perforated field plate are readable while the sliding plate is inserted. This facilitates the assignment of the sample to a position within the perforated field plate. The transfer plate usually has the same dimensions as the perforated field plate so that an aligned arrangement of the holes can be achieved through simple overlap of the edges of the hole plates on both sides. Afterwards, the sliding plate is usually pulled out of the sliding guide between the perforated field plate and the transfer plate so that the samples fall down into the holes of the perforated field plate.

The analytical device is usually aligned in a way that the holes of the perforated field plate extend in the vertical direction so that both the transfer from the transfer plate onto the perforated field plate as well as the ejection of the sample in the direction onto the reactor can take place by means of the gravitational force. Contrary to this movement direction, gas usually also flows through the ejection openings so that ambient air is prevented reliably from flowing with the sample into the reactor for catalytic combustion and from distorting the result of the sample there. The analytical device usually has a valve in order to switch between an oxygen flow in the line and an inert gas flow so that the sample can be ejected without any contamination during the inert gas flow and that a switch to oxygen gas can take place afterwards in order to achieve a residue-free catalytic combustion.

The transfer plate can have a hole field that is formed in accordance with the first and the second hole field and that aligns with this hole field so that both samples to be processed in the usual order as well as samples with a higher priority can be loaded after positioning of the transfer plate.

According to a preferred further development of the present invention, a sliding piston that is guided in a sealing way in an extending cylinder is provided on the bottom side of the base. The sliding piston has a receptacle hole that has regularly the same axial alignment as the ejection opening. This receptacle hole can be moved cyclically back and forth between a first position and a second position. In the first position, the receptacle hole aligns with the ejection opening. In the second position, the receptacle hole aligns with a line section of the line for the inert gas, in particular the helium, and the oxygen that usually leads directly to the reactor for the catalytic combustion in a strictly vertical extension.

Therefore, the sample that is shifted from the base into the ejection opening can arrive directly at the reactor. The sliding piston is usually held in the extending cylinder in a sealing way. For this purpose, grooves, which hold sealing rings that interact with the internal circumferential surface of the extending cylinder, are usually left out on the sliding piston directly next to the receptacle hole. Already the extending cylinder is usually connected to a source at least for the inert gas to prevent undesired entry of atmospheric air into the analytical device through the ejection opening. This way, the mentioned extending cylinder forms a lock with the sliding piston absorbed in it.

According to a preferred further development of the present invention, the base has a display window. Thanks to this display window, the receptacle hole can be viewed through the base in the second position. Therefore, it can be observed that the sample is (has) actually (been) ejected into the line section of the line when the receptacle hole is in the second position. The display window thereby seals the area above the receptacle hole so that an entry of ambient air through the display window into the receptacle hole and to the reactor is prevented. The display window is usually provided flushly and free of indentations with the surface of the base so that also samples can be relocated over the display window without parts of the samples being caught in the area of the display window.

According to a preferred further development of the present invention, a camera that points towards the ejection opening and/or the display window is provided. The camera is usually connected to a central logic unit and optically monitors the ejection of the sample through the ejection opening and/or the transfer of the sample in the second position of the receptacle hole into the line section.

Figure 2:
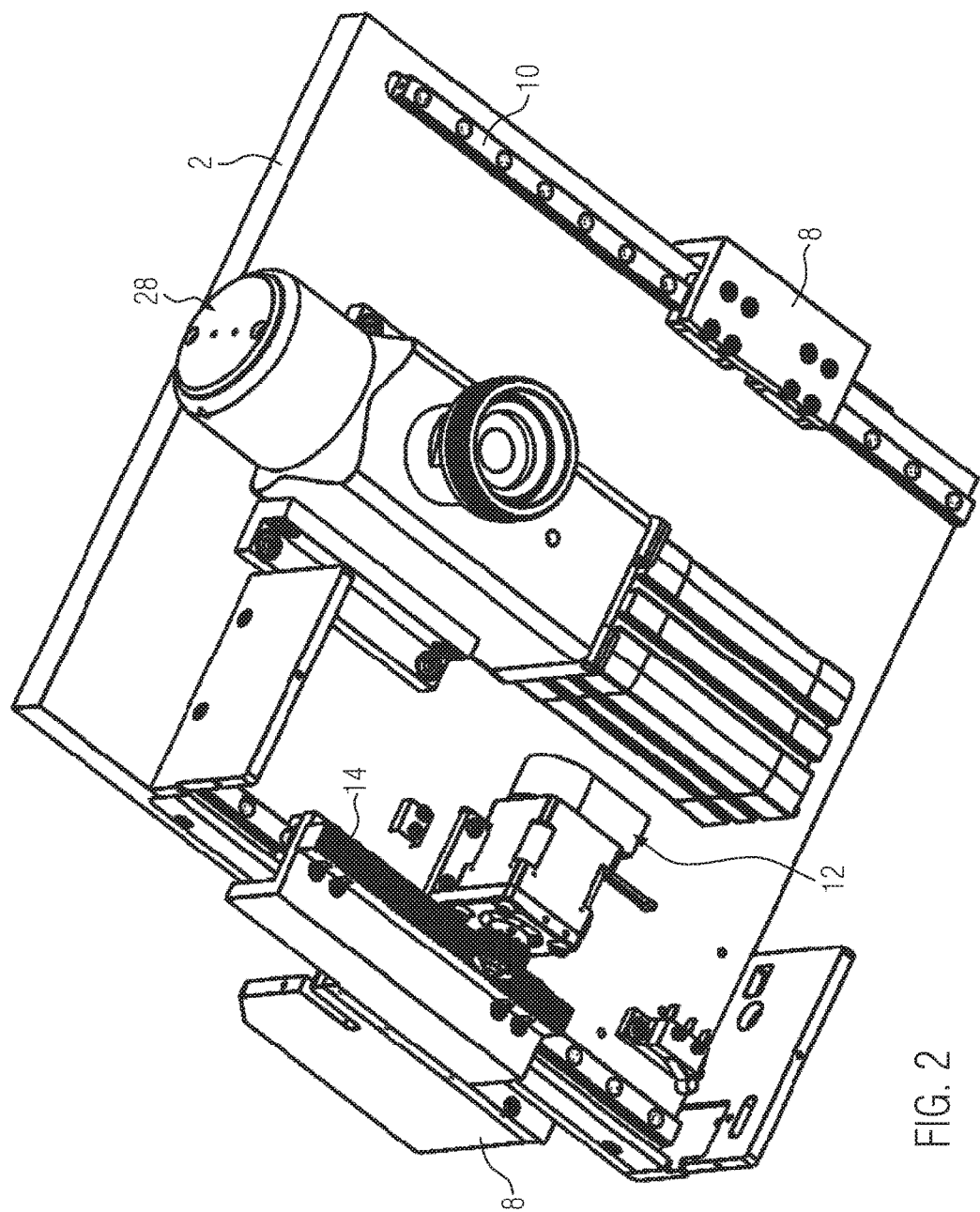
FIG. 2 shows a perspective view of the bottom side of the embodiment.
Figure 3:
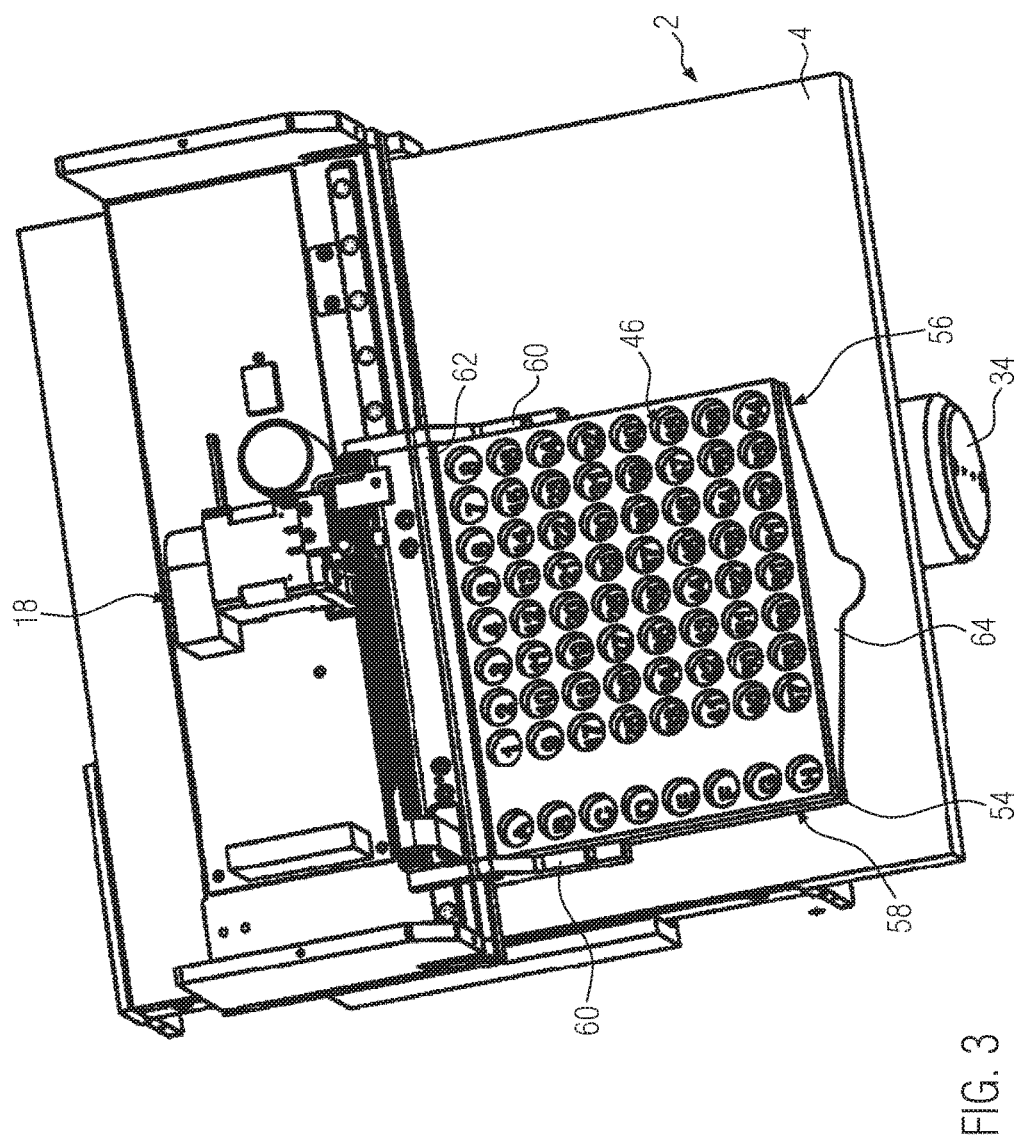
FIG. 3 shows a perspective top view of the top side of the embodiment.
Figure 4:
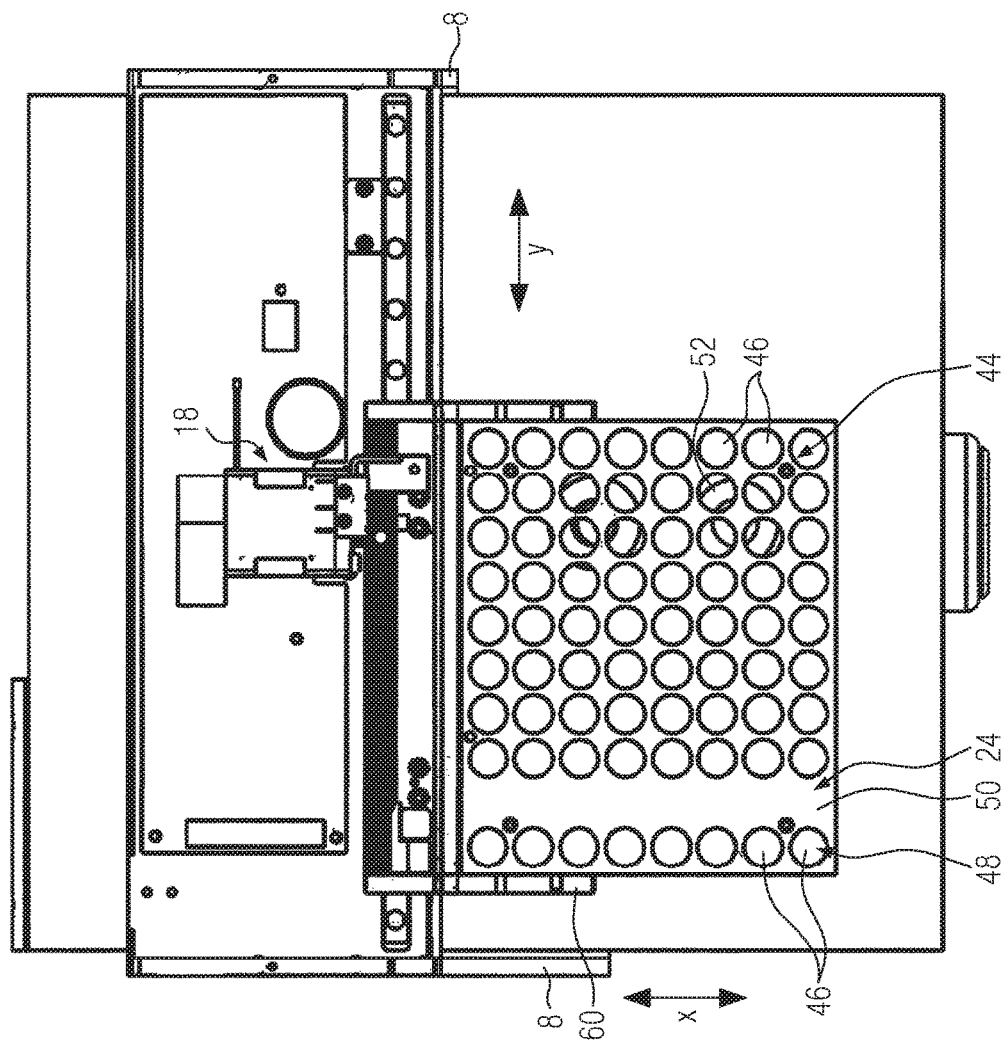
FIG. 4 shows a top view of the embodiment while the transfer plate is removed.
Figure 5:
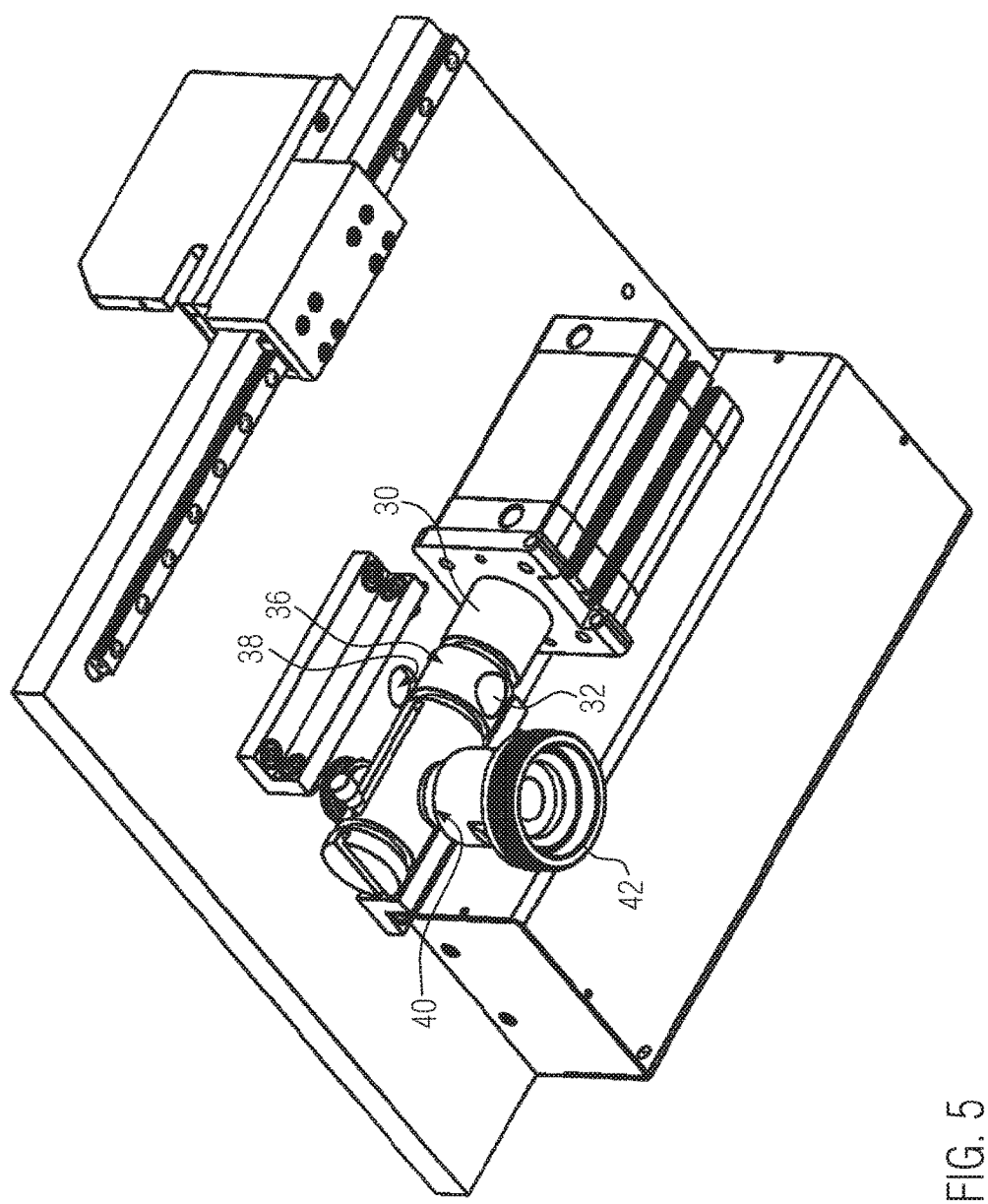
FIG. 5 shows a perspective bottom view of the embodiment, whereby parts of the extending cylinder are drawn transparently.
Figure 6:
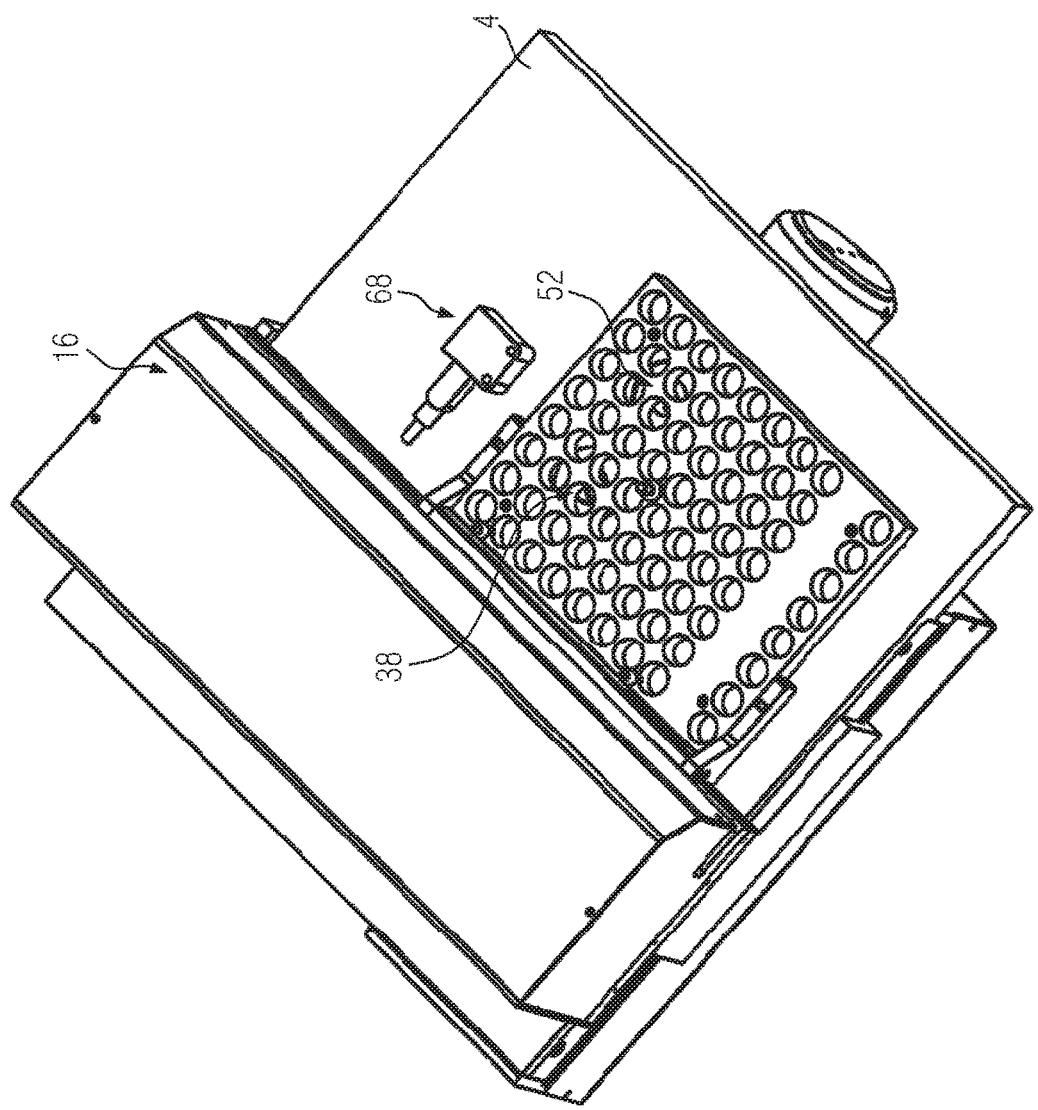
FIG. 6 shows a perspective top view of the top side of a slightly modified second embodiment.
Figure 7:
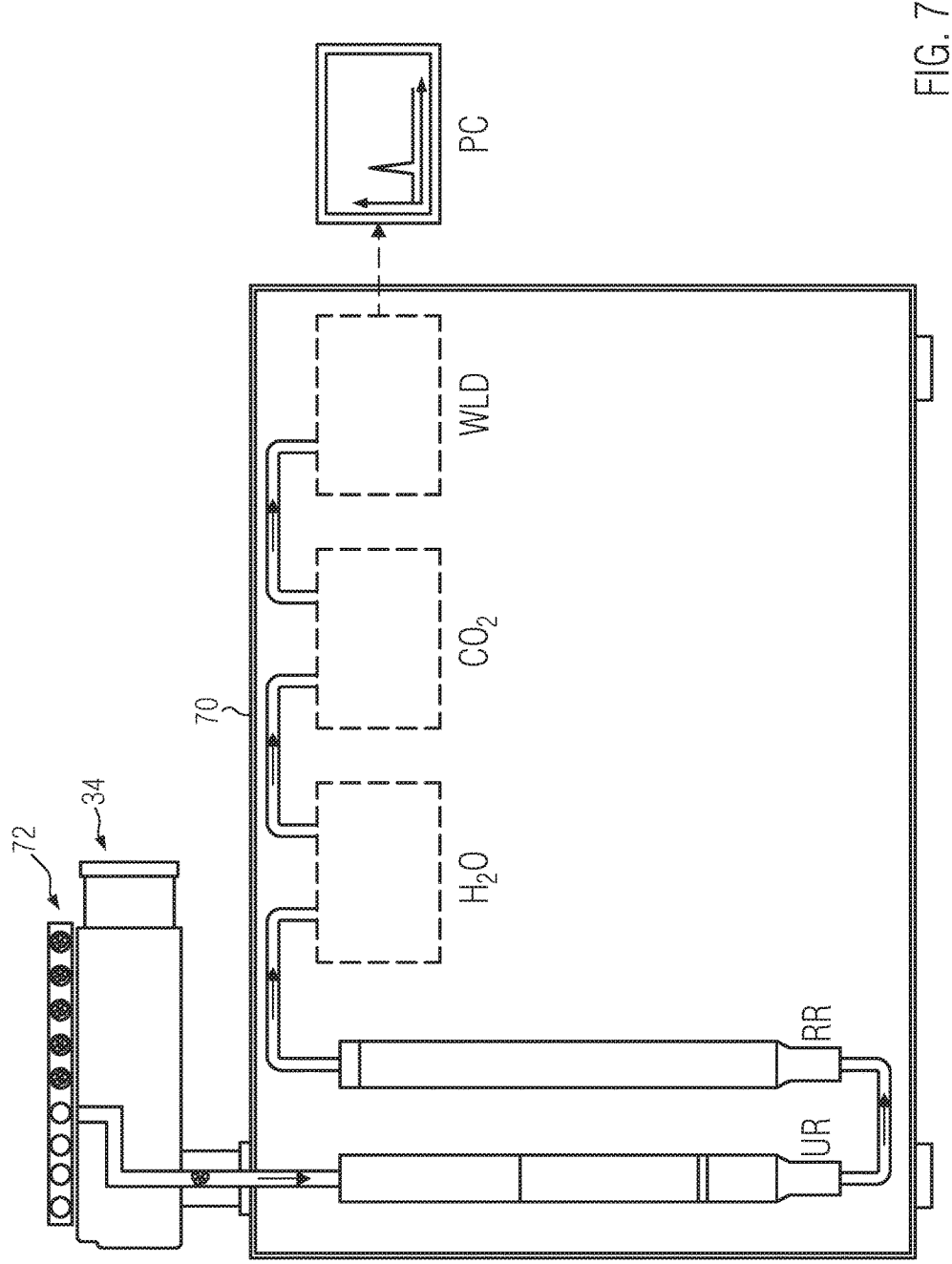
FIG. 7 shows a schematic display of the essential components of an elementary analysis according to Dumas.

Further details and benefits of the present invention are provided by the following embodiment in connection with the drawing. The drawing shows:

FIG. 1 a perspective side view of the top side of the embodiment;

FIG. 2 a perspective view of the bottom side of the embodiment;

FIG. 3 a perspective top view of the top side of the embodiment;

FIG. 4 a top view of the embodiment while the transfer plate is removed;

FIG. 5 a perspective bottom view of the embodiment, whereby parts of the extending cylinder are drawn transparently;

FIG. 6 a perspective top view of the top side of a slightly modified second embodiment, and FIG. 7 a schematic display of the essential components of an elementary analysis according to Dumas.

FIGS. 1 and 2 display the essential parts of the embodiment. It comprises a base plate 2 that forms an even base 4 and that guides a crossbeam 6, which is movable in the direction of the directional arrow X and connected to the base plate 2, on the top side. For this purpose, the crossbeam 6 has lateral legs 8 that encompass the base plate 2 (cf. FIG. 2). There, longitudinal guides 10 as well as a first drive 12, which meshes by means of a gear wheel with a first gear rack 14 that is fixed on one of the legs 8, is provided. This creates the possibility of moving the crossbeam 6 in a first direction, i.e. the X-direction in relation to the base 4.

The crossbeam 6 has a cover 16 that covers a second drive 18 that meshes by means of a gear wheel with a second gear beam 20 that is connected to a holder 22 for a perforated field plate 24. The crossbeam 6 forms a transversal guide 26 through which the holder 22 is movable in the second direction, i.e. in the X-Y-direction indicated in FIG. 1. The two drives 12, 18 are coupled through a controlling connection with a logic unit that controls the two drives 12, 18 in such a way that the perforated field plate 24 is held and/or arranged in a predetermined position.

FIG. 2 shows a lock for introducing a sample that is marked with reference sign 28. Details of this lock 28 are displayed in FIG. 5. The lock 28 has (cf. FIG. 5) a movable sliding piston 30 that is interspersed by the receptacle hole 32 and that is held movably in an extending cylinder 34. The extending cylinder 34 has a feed opening 36 that aligns with an ejection opening left out in the base plate 38, and a discharge opening 40 that aligns with a line section 42 that is connected to the extending cylinder 34 and that is adapted for sealed screwing of a reactor for catalytic combustion that is not shown.

The further components that form the analytical device as such are predominantly not shown. Insofar, reference is made to the EP 1 586 895 A1 that discloses the essential components for an analytical device, in particular an analytical device for the analysis of nitrogen in samples. In this context, reference is made to this disclosure.

The perforated field plate 24 shown in FIG. 4 has a first hole field 44 with multiple rows of holes 46 that are provided at even distances in relation to each other and a second hole field 48 that is formed by a single row of holes 46. An enlarged crosspiece 50 is provided between the two hole fields 44, 48.

Further, FIG. 4 displays the ejection opening 38 in the viewing direction behind the perforated field plate 24 as well as a display window that is marked with reference sign 52 and that allows for a view through the wall of the extending cylinder 34 onto the receptacle hole 32 in the second position of the sliding piston 30 in which the receptacle hole 32 aligns with the line section 42.

As shown in FIG. 4, the crosspiece 50 has a greater width in relation to the connecting bridges between rows of the first hole field 44. The width of the crosspiece 50 is thereby chosen in a way that it exceeds the diameter of the ejection opening 38 slightly and that it is consequently suitable to cover the ejection opening 38.

FIGS. 1 and 3 show the first embodiment together with a transfer plate 54 that is laid onto the perforated field plate 24 in the mentioned FIG. The transfer plate 54 has the same dimensions as the perforated field plate 24. Also, the transfer plate 54 has first and second transfer hole fields 56, 58 whose holes are provided with the same distance and/or grid pattern as the holes of the first and second hole field 44, 48 of the perforated field plate 24. For easier positioning, the holding arms 60, which hold the perforated field plate 24 and which are connected to the second gear rack 20, as well as a carrier 62 that extends at a right angle to such holding arms are provided with a height above the base 4 that corresponds approximately to the height of the perforated field plate 24 and the transfer plate 54. This creates a receptacle opening into which the transfer plate 54 can be inserted for exact overlap with the holes on both sides of the perforated field plate 24 and the transfer plate 54 by means of arranging the plates 24, 54 on top of each other. The holding arms 60 and the carrier 62 are connected to the second drive. FIG. 1 further shows a sliding plate 64 that is provided on top of the perforated field plate 24 and that is held movably in a sliding guide 66 that is left out on the transfer plate 54. The sliding plate 64 closes the holes of the transfer hole fields 56, 58 on the bottom side. Therefore, the transfer plate 54 can at first be loaded at a laboratory facility and then be arranged with the sliding plate 64 in the position above the perforated field plate 24 and aligned to such perforated field plate. Afterwards, the sliding plate 64 is pulled whereby the samples fall respectively from the holes of the transfer plate 54 into the corresponding holes 46 of the perforated field plate 24.

As shown in particular in FIG. 3, sample positions are inscribed on the top side of the sliding plate 64 so that sample positions are assigned to every single hole of the transfer plate 54 and hence every single hole of the perforated field plate 24. In this context, the sample positions 1 to 64 correspond to the positions of the first hole field. These holes 46 have constant transversal and longitudinal distances, i.e. constant spacings both in the X-as well as the Y-direction. The holes A-H are holes of the second hole field 2, which are only provided successively in the X-direction but there with the distance of the holes 46 of the first hole field 44.

After loading of the perforated field plate 24 by means of pulling the sliding plate 64, the transfer plate 54 is lifted off in order to load such transfer plate again while the automated analysis is performed by the embodiment. For this purpose, the drives 12 and 18 are operated in a controlled way in order to bring the perforated field plate 24 with a selected hole 46 on top of the ejection opening 38. Therefore, the sample is ejected out of the corresponding hole 46, i.e. into the receptacle hole 32 of the sliding piston 30 that is in the first position. Then, the sliding piston 30 is displaced into the extending cylinder 34 so that the receptacle hole 32 aligns with the line section 42. Due to the gravitational force, the sample is consequently ejected through the discharge opening 40 into the line section 42 and hence into the reactor for catalytic combustion. The sample is burnt by adding oxygen in a way that is known per se. The combustion gases are treated to separate for example water. Subsequently, the combustion gases are fed to the adsorber so that the ingredients that are of interest for the analysis can be separated and measured by means of the detector.

FIG. 6 shows an alternative embodiment with a camera 68 that is provided above the base 4 and in whose field of view there is both the ejection opening 38 as well as the display window 52. The camera 68 is usually provided in the axial extension of the axis of the display window 52 and can consequently also record the line section 42 optically. The camera 68 is connected to the central logic unit. It can detect both the ejection of the sample out of the perforated field plate 24 through the ejection opening 38 as well as the ejection of the sample out of the receptacle hole 32 into the line section 42.

A gas line through which inert gas, for example helium, can be led to the inside of the extending cylinder 34 is connected to the extending cylinder 34. Therefore, it is possible to remove ambient air that is originally contained in the extending cylinder 34 through the ejection opening 38 prior to the analysis in order to create an inert gas atmosphere within the analytical device that does not contain the substance to be measured/the element to be determined in the sample.

The further way of the sample from the line section 42 is schematically displayed in FIG. 6. The sample falls into a reactor UR for catalytic combustion. The gases formed in this process are fed into a reduction reactor RR. Then, water that is contained in the combustion gas is absorbed (H). $CO_2$ that is contained in the gas is subsequently removed from the gas (C). Finally, the nitrogen content is measured (at S) and the measured value is analyzed and emitted by a computer (PC). The frame marked with reference sign 70 in FIG. 7 thereby illustrates those features of the analytical device that are located within a housing, whereby the extending cylinder 34 with the sample holder described previously with reference to FIGS. 1 to 6 is provided on the top side of the housing 70, whereby the sample holder is indicated only schematically by a perforated disc (72).

REFERENCE SIGN LIST

2 Base plate
4 Base
6 Crossbeam
8 Leg
10 Longitudinal guide
12 First drive
14 First gear rack
16 Cover
18 Second drive
20 Second gear rack
22 Holder
24 Perforated field plate
26 Transversal guide
28 Lock
30 Sliding piston
32 Receptacle hole
34 Extending cylinder
36 Feed opening
38 Ejection opening
40 Discharge opening
42 Line section
44 First hole field
46 Hole
48 Second hole field
50 Enlarged crosspiece
52 Display window
54 Transfer plate
56 First transfer hole field
58 Second transfer hole field
60 Holding arms
62 Carrier 64 Sliding plate
66 Sliding guide
68 Camera
70 Frame
72 Perforated disc

The invention claimed is:

1. An analytical device for elementary analysis comprising:
   a sample holder configured to hold at least one sample therein, the sample holder comprising a perforated field plate,
   a base comprising an ejection opening to eject the at least one sample,
   at least one drive device operatively connected to the perforated field plate and the base to move the perforated field plate on the base,
   a line for oxygen and inert gas,
   a reactor for catalytic combustion of the at least one sample,
   a reduction reactor provided downstream of the reactor,
   an adsorber provided downstream of the reduction reactor,
   a detector provided downstream of the absorber, and
   a logic unit for processing of the data transmitted by the detector,
   wherein the perforated field plate is movable on the base by the at least one drive device to be translatable in a Cartesian X-Y coordinate system.

2. The analytical device according to claim 1, wherein the perforated field plate comprises a first hole field and a second hole field that are separated from each other by means of an enlarged crosspiece.

3. The analytical device according to claim 1, wherein the perforated field plate is held on a crossbeam, the crossbeam being movable in a first direction (X) in relation to a base plate that forms the base and encompassing the base plate, wherein the perforated field plate is held movably in the longitudinal direction of the crossbeam in relation to such crossbeam.

4. The analytical device according to claim 1, wherein a transfer plate that is equipped with a first transfer hole field that corresponds at least to the first hole field to which a sliding plate is assigned for closing the transfer plate, which can be pulled out between the perforated field plate and the transfer plate after putting the transfer plate onto the perforated field plate, on the bottom side.

5. The analytical device according to claim 1, wherein a sliding piston, which is provided on the bottom side of the base and guided in a sealing way in an extending cylinder, with a receptacle hole that is cyclically movable between a first position, in which the receptacle hole is arranged in alignment with the ejection opening, and a second position in which the receptacle hole is disposed in alignment with a line section of the line for oxygen and inert gas, which leads to the reactor.

6. The analytical device according to claim 5, wherein the base comprises a display window to check the positioning of the receptacle hole in the second position.

7. The analytical device according claim 6, further comprising a camera that points towards the ejection opening and/or the display window.

8. A sample holder of an analytical device for elementary analysis, the sample holder being configured to hold at least one sample therein, the sample holder comprising:
   a perforated field plate, and
   a base comprising an ejection opening to eject the at least one sample,
   wherein the perforated field plate is movable on the base by a drive to be translatable in a Cartesian X-Y coordinate system.

9. The sample holder according to claim 8, wherein the perforated field plate comprises a first hole field and a second hole field that are separated from each other by means of an enlarged crosspiece.

10. The sample holder according to claim 8, wherein the perforated field plate is held on a crossbeam, the crossbeam being movable in a first direction (X) in relation to a base plate that forms the base and encompassing the base plate, wherein the perforated field plate is held movably in the longitudinal direction of the crossbeam in relation to such crossbeam.

11. The sample holder according to claim 9, wherein a transfer plate that is equipped with a first transfer hole field that corresponds at least to the first hole field to which a sliding plate is assigned for closing the transfer plate, which can be pulled out between the perforated field plate and the transfer plate after putting the transfer plate onto the perforated field plate, on the bottom side.

12. The sample holder according to claim 8, wherein a sliding piston is provided on the bottom side of the base and guided in a sealing way in an extending cylinder, with a receptacle hole that is cyclically movable between a first position, in which the receptacle hole is arranged in alignment with the ejection opening, and a second position in which the receptacle hole is disposed in alignment with a line section of a line that leads to a reactor.

13. The sample holder according to claim 12, wherein the base comprises a display window to check the positioning of the receptacle hole in the second position.

14. The sample holder according to claim 13, further comprising a camera that points towards the display window.

15. The sample holder according to claim 8, further comprising a camera that points towards the ejection opening.

* * * * *

UNITED STATES PATENT AND TRADEMARK OFFICE
CERTIFICATE OF CORRECTION

PATENT NO. : 10,274,442 B2
APPLICATION NO. : 15/191926
DATED : April 30, 2019
INVENTOR(S) : Jan Macke It is certified that error appears in the above-identified patent and that said Letters Patent is hereby corrected as shown below:

In the Claims

Column 10, Line 7, Claim 7, after "according" insert -- to --

Signed and Sealed this
Thirtieth Day of July, 2019

Andrei Iancu
*Director of the United States Patent and Trademark Office*